United States Patent
Baumgartner et al.

(10) Patent No.: US 10,351,797 B2
(45) Date of Patent: Jul. 16, 2019

(54) ENAMINE AND/OR AMINAL FRAGRANCE PRECURSORS DERIVED FROM (E/Z)-9-HYDROXY-5,9-DI-METHYLDEC-4-ENAL

(71) Applicant: GIVAUDAN SA, Vernier (CH)

(72) Inventors: Corinne Baumgartner, Fällanden (CH); Veronika Zelenay, Dübendorf (CH)

(73) Assignee: GIVAUDAN SA, Vernier (CH)

(*) Notice: Subject to any disclaimer, the term of this patent is extended or adjusted under 35 U.S.C. 154(b) by 0 days.

(21) Appl. No.: 15/528,181

(22) PCT Filed: Dec. 8, 2015

(86) PCT No.: PCT/EP2015/079017
§ 371 (c)(1),
(2) Date: May 19, 2017

(87) PCT Pub. No.: WO2016/091899
PCT Pub. Date: Jun. 16, 2016

(65) Prior Publication Data
US 2017/0362533 A1    Dec. 21, 2017

(30) Foreign Application Priority Data

Dec. 9, 2014 (GB) .................................. 1421838.2

(51) Int. Cl.
*C11B 9/00* (2006.01)
*C07C 229/56* (2006.01)
*C11D 3/50* (2006.01)

(52) U.S. Cl.
CPC .......... *C11B 9/0061* (2013.01); *C07C 229/56* (2013.01); *C11B 9/003* (2013.01); *C11B 9/0015* (2013.01); *C11D 3/50* (2013.01)

(58) Field of Classification Search
None
See application file for complete search history.

(56) References Cited

U.S. PATENT DOCUMENTS

| | | |
|---|---|---|
| 3,953,518 A | 4/1976 | Wehrli |
| 4,057,515 A | 11/1977 | Boelens et al. |
| 4,271,048 A | 6/1981 | Buechi et al. |
| 5,155,095 A | 10/1992 | Blanc et al. |
| 9,469,590 B2 | 10/2016 | Alchenberger et al. |

FOREIGN PATENT DOCUMENTS

| | | |
|---|---|---|
| GB | 981702 | 1/1965 |
| GB | 981702 A2 | 1/1965 |
| GB | 1158791 | 7/1969 |
| GB | 1414759 | 11/1975 |
| GB | 2515128 A | 12/2014 |
| JP | 5291815 A | 8/1977 |
| WO | 2008087609 A2 | 7/2008 |
| WO | 2014198709 A1 | 12/2014 |
| WO | 2015181257 A2 | 12/2015 |

OTHER PUBLICATIONS

International Search Report and Written Opinion of the International Searching Authority for corresponding application PCT/EP2015/079017 dated Mar. 9, 2016.
GB Search Report for corresponding application GB1421838.2 dated Sep. 15, 2015.
GB Search Report for GB 1313641.1 dated Jan. 29, 2014.
Anonymous, "Opinion of the Scientific Committee on Cosmetic Products and Non-Food Products Intended for Consumers Concerning Hydroxyisohexyl 3-Cyclohexene Carboxaldehyde", Dec. 2003, XP002726813, retrieved from the Internet, URL: http://ec.europa.eu/health/archive/ph_risk/committees/sccp/documents/out249_en.pdf.
International Search Report for corresponding application PCT/EP2014/062002 dated Aug. 4, 2014.
Written Opinion of the international Searching Authority for PCT/EP2014/062002 dated Aug. 4, 2014.

*Primary Examiner* — Arrie L Reuther
(74) *Attorney, Agent, or Firm* — Norris McLaughlin, PA

(57) ABSTRACT

A fragrance precursor of (E/Z)-9-hydroxy-5,9-dimethyldec-4-enal, comprising at least an enamine and/or an aminal as reaction product of (E/Z)-9-hydroxy-5,9-dimethyldec-4-enal (compound according to formula (I)) and a primary and/or secondary amine

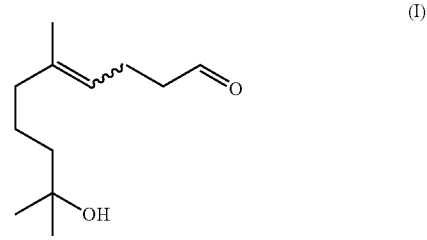

(I)

useful as a perfume ingredient.

20 Claims, No Drawings

ENAMINE AND/OR AMINAL FRAGRANCE PRECURSORS DERIVED FROM (E/Z)-9-HYDROXY-5,9-DI-METHYLDEC-4-ENAL

This is an application filed under 35 USC 371 of PCT/EP2015/079017, filed 8 Dec. 2015, which in turn was based on GB 1421838.2 filed 9 Dec. 2014. This application claims the full priority benefit to the foregoing applications and also incorporates them here by reference as if set forth herein.

The present invention relates to fragrance precursors derived from a reaction between an amine and (E/Z)-9-hydroxy-5,9-dimethyldec-4-enal. These fragrance precursors are able to release (E/Z)-9-hydroxy-5,9-dimethyldec-4-enal Furthermore, the invention relates to the use of such precursors in perfume preparations. In particular, the invention relates to fragrance precursors or perfume preparations containing said precursors that release fragrance with muguet (lily of the valley) odour characteristics. Still more particularly, the invention relates to said perfume preparations that contain no, or substantially no, Lyral™. The invention further relates to methods of making said perfume precursors and perfume preparations, as well as the use of said perfume precursors and perfume preparations in fine fragrances and consumer products, such as personal care and household care products. The invention also relates to said fine fragrances and consumer products containing said perfume precursors and perfume preparations.

Compounds having muguet odour characteristics are very sought after as perfume ingredients. These compounds are important ingredients in floral bases and can act as harmonizers across many types of fragrance creations. Compounds of this type are used widely in personal care and consumer care products, as well as in fine perfumery, to generate pleasant odours or to mask unpleasant odours.

An excellent perfume ingredient widely valued for its muguet odour note is 4(4-hydroxy-4-methylpentyl) 3-cyclohexene carboxaldehyde, also known as Cyclohexal (Lyral™). This compound has found wide use in fine perfumery as well as in personal and household care products. However according to findings of the European Scientific Committee for Consumer Safety (SCCS) it has allergenic concerns and at the present time may be subject to regulatory action in the EU.

Recently, applicant has found a novel compound (E/Z)-9-hydroxy-5,9-dimethyldec-4-enal that can be employed as a perfume ingredient in perfume compositions and fine fragrances and consumer products. The novel compound possesses desirable classic floral, green muguet odour characteristics and may be perceived and recognised by perfumers as being very reminiscent of the odour of cyclohexal (Lyral™) and so can serve as a simple replacement for Lyral™. Details of this invention are disclosed in international patent application PCT/EP2014/062002, which is hereby incorporated by reference Perfumed products such as cleaning or laundry products comprising Lyral™ are well-known in the art.

However, it is known that fragrances can be altered through degradation caused by interaction with air when incorporated in certain consumer product bases, where alkalinity, acidity, the presence of oxidizing agents, such as hypochlorite salts, or other base components may lead to chemical degradation of the fragrance. In addition, volatile fragrances tend to be dissipated with time. Furthermore, when used in cleaning or laundry products, the deposition of the fragrance on a treated substrate is diminished by the washing and/or rinsing procedure.

Nevertheless, it is desired by consumers to have products that can be stored over time and still giving a constant perfume impression. In particular, the impact of volatile components is to be retained. Furthermore, it is desired that such products create a long-lasting pleasing fragrance slowly emitting from the treated substrate over time.

Therefore, it is an objective of the present invention to provide a system which is capable of releasing the above mentioned Lyral™ type fragrance constantly over time and providing a long-lasting release of said fragrance.

It is another objective of the present invention to increase the substantivity of (E/Z)-9-hydroxy-5,9-dimethyldec-4-enal, in particular in consumer product applications, especially in the so-called rinse off applications, like fabric softener or conditioner, as well as in hair shampoo or fabric detergents.

Applicant has found that reaction products of a primary and/or secondary amine compound and (E/Z)-9-hydroxy-5,9-dimethyldec-4-enal can serve as fragrance precursors of (E/Z)-9-hydroxy-5,9-dimethyldec-4-enal. These fragrance precursors provide a delayed release of (E/Z)-9-hydroxy-5,9-dimethyldec-4-enal over a longer period of time than by the use of the fragrance itself.

A reaction of a primary and/or secondary amine compound and (E/Z)-9-hydroxy-5,9-dimethyldec-4-enal may give several reaction products, for examples imines, Schiff bases, hemi-aminals, aminals and enamines. Furthermore, several polymeric and oligomeric products may be formed.

When studying the reaction products of methyl ortho-aminobenzoate (methyl anthranilate) and (E/Z)-9-hydroxy-5,9-dimethyldec-4-enal in a molar ratio in a range from 4:1 to 1:2, applicant surprisingly found that the main reaction product is not an imine or a Schiff base, characterized by a carbon-nitrogen double bond. In contrast, these reaction mixtures comprise at least the corresponding aminal and/or enamine.

Accordingly, the invention provides in a first aspect a fragrance precursor comprising at least the corresponding aminal and/or enamine of the compound of formula I. Such a fragrance precursor can be obtained by a reaction of a primary and/or secondary amine compound and (E/Z)-9-hydroxy-5,9-dimethyldec-4-enal (compound of formula I)

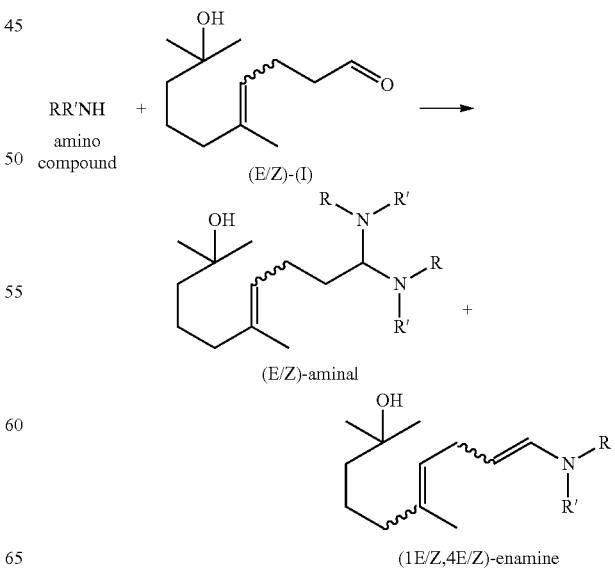

However, under modified reaction conditions, for example in reactions with an amine compound and the aldehyde in amended molar ratios and/or depending on the nature of the amino compound, further products in different ratios may be formed, for example the corresponding imine or Schiff base or the hemi-aminal.

The aminal is a bis-adduct of the amino compound to the compound of formula I. It is obtained as a mixture of E/Z-isomers, as indicated by the wiggled bond. The enamine is a mono-adduct of the amino compound to the compound of formula I, characterized by a newly formed carbon-carbon double bond, leading to a structure with two double bonds. The enamine is obtained as a mixture of 1E/Z,4E/Z-isomers, as indicated by the wiggled bonds.

Primary amines with the general formula R—NH$_2$ and secondary amines with the general formula R—NHR' are able to react in the described manner. R and R' represent substituents such as linear or branched, saturated or unsaturated alkyl groups or further substituted or unsubstituted aryl groups. In case of a secondary amine, the substituents R and R' may form a ring system.

The said fragrance precursors are able to release (E/Z)-9-hydroxy-5,9-dimethyldec-4-enal, a compound with substantially similar odour characteristics and performance characteristics as Lyral™. The precursors provide an improved fragrance intensity and a long-lasting release (also known as substantivity) of (E/Z)-9-hydroxy-5,9-dimethyldec-4-enal.

According to the present invention, a fragrance precursor is a substance that is not itself a final fragrance, but which, in particular circumstances will break down to give at least one desired fragrant substance. The fragrance precursor will release the desired fragrance for example by hydrolysis with air moisture or water. The release can also be caused by exposure to light or oxygen, pH change and enzymatic activity.

The fragrance precursor itself can be odourless. Alternatively, the precursor may be an odorant on its own.

Usually, the fragrance precursor can be obtained by a reaction of (E/Z)-9-hydroxy-5,9-dimethyldec-4-enal and one primary and/or secondary amine compound. In a particular embodiment, a fragrance precursor can be obtained by a reaction of (E/Z)-9-hydroxy-5,9-dimethyldec-4-enal and a mixture of at least two primary and/or secondary amine compounds.

It is preferred to use a fragrance precursor as a prepared compound in a perfume mixture. However, in another aspect of the invention, it is possible to form said fragrance precursor directly in the perfume mixture by adding a primary and/or secondary amine compound and (E/Z)-9-hydroxy-5,9-dimethyldec-4-enal in a molar ratio in a range from 4:1 to 1:100 into the perfume mixture.

Preferably, the primary and/or secondary amine compound is selected from the group consisting of aromatic amines: methyl 2-aminobenzoate (methyl anthranilate), ethyl 2-aminobenzoate, 2-amino-acetophenone, ethyl 4-aminobenzoate, ortho, meta or para aminobenzoates of formula II (wherein R$^1$=C1-C12 linear or branched alkyl, alkenyl, cycloalkyl, cycloalkenyl or alkylaryl and R$^2$=H, Me, Et), 1-phenylethylamine, 2-phenylethylamine, 4,4'-methylenedianiline, benzylamine;

primary or secondary aliphatic amines: C8-C30 linear or branched alkylamines or alkyldiamines (e.g. octylamine, dodecylamine, tridecylamine (CAS: 86089-17-0), octadecylamine, nonan-2-amine, undecan-2-amine, 4-ethylcyclohexylamine, 9-octadecenylamine, dihexylamine, dicyclohexylamine, di-(2-ethylhexyl)amine, ditridecylamine, octamethylenediamine, 4,4'-diaminodicyclohexylmethane, 3,3'-dimethyl-4,4'diamino-dicyclohexylmethane), 1,4-diaminocyclohexane, 1,12-diaminododecane, isophorone diamine, 1,3-bis-(aminomethyl)cyclohexane, 1,3-bis-(aminoethyl)cyclohexane, aminoalkylpiperazines (e.g. 1,4-bis-(3-aminopropyl)piperazine), glucamines;

etheramines: 2-alkyloxyethylamines (e.g. 2-methoxyethylamine), 3-alkyloxypropylamines (e.g. 3-methoxypropylamine, 3-ethoxypropylamine, 3-(2-ethylhexoxy)propylamine), 4,7,10-trioxatridecane-1,13-diamine, 4,9-dioxadodecane-1,12-diamine, di-(2-methoxyethyl)amine;

ethylene- and propylene-amines: 2-(diethylamino)ethylamine, 2-(diisopropylamino)ethylamine, diethylenetriamine, triethylenetetramine, tetraethylenepentamine, 2,2',2"-triaminotriethylamine, N-(2-aminoethyl)ethanolamine, dipropylene triamine, 3-(dimethylamino)propylamine, 3-(alkylamino)propylamines (e.g. 3-(cyclohexylamino)-propylamine, 3-(oleylamino)-propylamine), 3-(2-aminoethylamino)-propylamine, N,N-bis-(3-aminopropyl)methylamine, linear or branched bis-(aminoalkyl) alkyldiamines (e.g. N,N'-bis-(3-aminopropyl)-ethylenediamine, N,N'-bis-(3-aminopropyl)-1,3-propanediamine);

amino acids and derivatives: tyrosine, tryptophane, lysine, glutamic acid, glutamine, aspartic acid, arginine, asparagine, phenylalanine, proline, glycine, serine, histidine, threonine, methionine, tyrosine ethylate, glycine methylate, tryptophane ethylate;

polyamines: primary and secondary polyetheramines (Jeffamine™), polyethyleneimines (Lupasol™), polypropyleneimines (Astramol™), polyamidoamines, polyamino acids (e.g. polylysine, cross-linked polylysine), polyvinylamines, poly(ethylene glycol) bis(amine), amino substituted polyvinylalcohols;

N-(3-aminopropyl)imidazole, nipecotamide, skatole and indole.

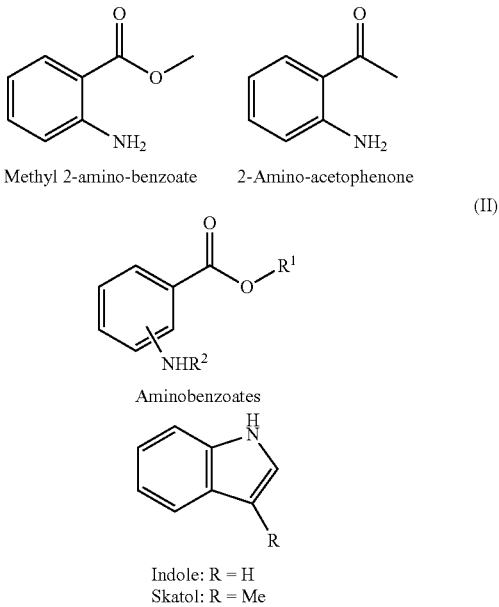

These preferred amine compounds are substantially odourless or have only slight but not significant odours, and so constitute substantially odourless materials. Alternatively, they are known or new perfume ingredients and can therefore contribute in a pleasant way to the odour properties of the overall fragrance, when released from the reaction mixture.

A particularly preferred amino compound is methyl ortho-aminobenzoate (methyl anthranilate). With that amino compound, an olfactively most attracting fragrance precursor may be obtained by the reaction of the amine compound and (E/Z)-9-hydroxy-5,9-dimethyldec-4-enal in a molar ratio in a range between 2:1 to 1:1. Such reaction mixtures give at least methyl 2-(((1E/Z, 4E/Z)-9-hydroxy-5,9-dimethyldeca-1,4-dien-1-yl)amino)benzoate and/or (E/Z)-Dimethyl 2,2'-((9-hydroxy-5,9-dimethyldec-4-ene-1,1-diyl)bis(azanediyl))dibenzoate.

Furthermore, the precursors are substantially odourless or have pleasant odour characteristics that may improve odour properties of the overall fragrance, respectively. It is important that the odour properties of the overall fragrance are not affected, or are not adversely affected, by the presence of the reaction product.

In another of its aspects, the invention provides the use of the described fragrance precursor, that is at least the aminal and/or enamine of (E/Z)-9-hydroxy-5,9-dimethyldec-4-enal, as a perfume ingredient.

Usually, the crude reaction mixture is used as said fragrance precursor. In a particular embodiment, the crude reaction mixture may be purified before use as fragrance precursor.

In particular, the precursor as perfume ingredient can release an ingredient with muguet odour characteristics.

The present invention provides a precursor that can release a single fragrance compound for a Lyral™ replacement. Such a replacement by a single fragrance might be cost-effective and convenient for a perfumer. The precursor releasing the compound of formula (I) provides perfumers with an eminently suitable surrogate for the valuable yet problematic Lyral™.

In a further aspect of the invention, there is provided a precursor suitable for replacement of Lyral™ precursors, in particular for the precursors made by a reaction of an amine and Lyral™, more particularly for precursors made by a reaction of methyl anthranilate and Lyral™, also known as Lyrantion™.

In another aspect of the invention there is provided a method of imparting a muguet odour characteristic to a perfume composition, said method comprising the step of incorporating a fragrance precursor releasing the compound of formula (I) into said perfume composition.

In yet another aspect of the invention there is provided a perfume composition comprising a fragrance precursor, that is an aminal and/or enamine of (E/Z)-9-hydroxy-5,9-dimethyldec-4-enal.

In yet another aspect of the invention there is provided a perfume composition possessing muguet odour characteristics comprising a fragrance precursor releasing a compound according to the formula (I).

A perfume composition according to the present invention can be made up entirely by the fragrance precursor, that is an aminal and/or enamine of (E/Z)-9-hydroxy-5,9-dimethyldec-4-enal. However, a perfume composition may also contain, in addition to the said fragrance precursor, one or more additional perfume ingredients.

The fragrance precursor, that is an aminal and/or enamine of (E/Z)-9-hydroxy-5,9-dimethyldec-4-enal, may be present in a perfume composition in any amount depending on the particular olfactive effect that a perfumer wishes to achieve. In a particular embodiment of the present invention, a perfume composition of the present invention may contain the fragrance precursor, that is an aminal and/or enamine of (E/Z)-9-hydroxy-5,9-dimethyldec-4-enal in an amount of 0.1 to 100% by weight of said composition.

It is particularly preferred, that the perfume composition further comprises (E/Z)-9-hydroxy-5,9-dimethyldec-4-enal. The mixture of the fragrance and a precursor releasing said fragrance ensures a constant and long-lasting fragrance impression over time.

The perfume composition may further comprise additional perfume ingredients. If one or more additional perfume ingredients are employed, they may be selected from any known perfume ingredients or from their precursor systems, respectively.

In particular, said perfume ingredients that may be employed in a perfume composition according to the invention include 3-(4-isobutyl-2-methylphenyl)propanal; 2-cyclohexylidene-2-phenylacetonitrile, e.g. PEONILE™; 4-(octahydro-4,7-methano-5H-inden-5-ylidene)butanal, e.g. DUPICAL™; 4-methyl-2-(2-methylpropyl)tetrahydro-2H-pyran-4-ol, e.g. FLOROSA™; and methyl 2-(2-hexyl-3-oxocyclopentyl)acetate, e. g. HEDIONE™.

Furthermore, perfume ingredients that may be employed in a perfume composition according to the invention include:

Natural ingredients, such as those selected from Iris, Mimosa, Ylang, Bergamot, jasmine and rose;

Synthetic muguet fragrance ingredients such as Cyclamen aldehyde (103-95-7), Hydroxycitronellal (107-75-5), Hydroxy Citronellal diethyl acetal (7779-94-4), Lilial (80-54-6), Cyclohexal (31906-04-4), Silvial (6658-48-6), Bourgeonal (18127-01-0), Florhydral (125109-85-5), and Cyclemax (7775-00-0);

Harmonic floral ingredients of the rose type such as ethyl phenyl alcohol (60-12-8), Dimethyl phenyl ethyl carbinol (103-05-9), Citronellol (106-22-9), Rhodinol (106-22-9), Acet. DMBC (151-05-3), Geraniol (106-24-1), Nerol (106-25-2), Nerolidol (7212-44-4), Mefrosol (55066-48-3), Peomosa (19819-98-8), citronellyl iso butyrate (97-89-2), and Majantol (103694-68-4);

Harmonic floral ingredients of the freesia type such as Linalool (78-70-6), Rossitol (215231-33-7), and Coranol (83926-73-2);

Harmonic floral ingredients of the lilac type such as Alc. Cinnamic alcohol (104-54-1), propyl phenyl alcohol (122-97-4) and Terpineol (8000-41-7);

Harmonic floral ingredients of the jasmine type such as benzyl acetate (140-11-4), Hedione (24851-98-7), Hexyl Cinnamic aldehyde (101-86-0), and Amyl Cinnamic aldehyde (122-40-7);

Harmonic floral ingredients of the muguet type such as Super Muguet (26330-65-4), Hydroxycitronellal dimethyl acetate (141-92-4), Magnol (92046-49-6), Mugetanol (63767-86-2), Mugesia (56836-93-2), Indole (120-72-9), and Indolene (67860-00-8);

Green harmonic ingredients such as cis 3 Hexenol (928-96-1), phenyl acetic aldehyde (122-78-1), Maceal (67845-30-1), cis 3 hexenyl acetate (3681-71-8), Acetal CD (29895-73-6), Precarone (74499-58-4), Mefranal (55066-49-4), Elintaal (40910-49-4), Glycolierral (68901-32-6), and Coranol (83926-73-2);

Fresh harmonic ingredients such as C11 undecelenic aldehyde (112-45-8), C11 undecylic aldehyde (112-44-7), C 10 aldehyde (112-31-2), C 12 MNA aldehyde (110-41-8), Tropional (1205-17-0), Citral (5392-40-5), Oxyde de Limette (73018-51-6), Florhydral (125109-85-5), Floralozone (67634-15-5), Dihydro Farnesal (51513-58-7), Dihydrofarnesol (51411-24-6), Adoxal (141-13-9), Citronellyl Oxyacetaldehyde (7492-67-3), Floral super (71077-31-1) and Dodecenal (4826-62-4);

Harmonic woody ingredients such as Irisone (8013-90-9) and methyl Ionone (1335-46-2);

Harmonic powdery ingredients such as Fixolide (21145-77-7), Thibetolide (106-02-5), Héliotropine (120-57-0) and Vanilline (121-33-5); and Diverse harmonic floral ingredients such as Phixia (107-75-5), Farnesal (19317-11-4), Farnesyle acetate (29548-30-9), Rhodinyl acetate (141-11-7), Cyclomethylene Citronellol (15760-18-6), Mayol (5502-75-0), Myraldyl acetate (72403-67-9), and Melonia (3613-30-7), wherein the CAS numbers of the molecules are provided in parentheses.

In addition to the aforementioned perfume ingredients that may be employed as being particularly complimentary to the odour characteristics of the compound of formula (I), other fragrance ingredients commonly used in perfumery may be employed, for example any of those ingredients described in "Perfume and Flavour Chemicals", S. Arctander, Allured Publishing Corporation, 1994, IL, USA, which is incorporated herein by reference, including essential oils, plant extracts, absolutes, resinoids, odourants obtained from natural products and the like. However, it is preferred that the perfume compositions contain no, or substantially no, Cyclohexal.

The perfume ingredients contained in said perfume compositions are described above, but of course, the perfume mixture may not be limited to the stated ingredients. In particular, perfume compositions may comprise adjuvants that are commonly employed in perfume compositions. The term "adjuvants" refers to ingredients that might be employed in a perfume composition for reasons not specifically related to the olfactive performance of said composition. For example, an adjuvant may be an ingredient that acts as an aid to processing a perfume ingredient or ingredients, or a composition containing said ingredient(s), or it may improve handling or storage of a perfume ingredient or composition containing same. It might also be an ingredient that provides additional benefits such as imparting colour or texture. It might also be an ingredient that imparts light resistance or chemical stability to one or more ingredients contained in a perfume ingredient or composition containing same. A detailed description of the nature and type of adjuvants commonly used in perfume compositions containing same cannot be exhaustive, but it has to be mentioned that said ingredients are well known to a person skilled in the art. Examples of adjuvants include solvents and co-solvents; surfactants and emulsifiers; viscosity and rheology modifiers; thickening and gelling agents; preservative materials; pigments, dyestuffs and colouring matters; extenders, fillers and reinforcing agents; stabilisers against the detrimental effects of heat and light, bulking agents, acidulants, buffering agents and antioxidants.

In a particular embodiment of the present invention a composition comprising a fragrance precursor, that is an aminal and/or enamine of (E/Z)-9-hydroxy-5,9-dimethyldec-4-enal, or perfume composition containing same, as herein defined, contains an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis (1,1-dimethylethyl)-4-methylphenol (BHT, CAS 128-37-0) and related phenols, hydroquinones (CAS 121-31-9). More specifically, Tinogard Q in triethyl citrate (TEC) can be preferentially used as an antioxidant of released (E/Z)-9-hydroxy-5,9-dimethyldec-4-enal. The antioxidants may be applied in levels of 0.01 to 3%, preferably 0.1 to 1.5% by weight of the fragrance precursor.

Applicant found that unless precautions are taken to prevent excessive oxidation of (E/Z)-9-hydroxy-5,9-dimethyldec-4-enal, undesirable levels of oxidation products can be produced. Accordingly, an anti-oxidant may be employed in combination with the fragrance precursor, that is an aminal and/or enamine of (E/Z)-9-hydroxy-5,9-dimethyldec-4-enal.

Furthermore, any one or more of the perfume ingredients or adjuvants employed in the present invention might be formulated in a delivery vehicle if desired to provide a desired effect. Delivery vehicles may include encapsulates. Alternatively, a delivery vehicle may be in the form of a solid support, e.g. a polymeric support material onto which one or more perfume ingredients or adjuvants may be chemically or physically bound. Still further, one or more perfume ingredients or adjuvants may be dissolved or dispersed in a matrix material, which serves to control the rate at which said ingredient or ingredients emanates therefrom. In yet an alternative embodiment, one or more ingredients or adjuvants may be supported on a porous substrate, such as a cyclodextrin or a zeolite or other inorganic material. In a still further embodiment, one or more perfume ingredients may be provided in the form of a pro-perfume or precursor, which will react in a suitable environment to release the perfume ingredient in a controlled manner.

Having regard to the foregoing, it will be appreciated that a perfume composition may be at least partly in solid form, in gel form, in foam form and/or liquid form. If it is present in solid form, it then it may take the form of granules, powders or tablets.

The reaction product of a primary and/or secondary amine compound and (E/Z)-9-hydroxy-5,9-dimethyldec-4-enal, or perfume compositions described herein, may be employed to add a characteristic odour, in particular a muguet odour, to all manner of personal care and household care compositions, that will be released with time.

According to another aspect of the present invention there is provided a method of imparting muguet odour characteristics to a composition comprising the step of adding to said composition a precursor releasing a compound according to formula (I) or a perfume composition containing said precursor.

A precursor as a perfume ingredient, or when used in perfume compositions can generate particularly substantive and long-lasting muguet odour characteristics.

Consumer products such as personal and household care compositions include, but are not limited to a textile treatment product, an ironing aid, a cleaning cloth, a laundry detergent, a cleaning product, in particular, for hard and/or soft surfaces, a household cleaner, a care product, a wash care product, a laundry care product, a room fragrancer, and air freshener, a conditioner, a colorant, a fabric conditioner, a conditioning substrate, a pharmaceutical, a crop protection product, a polish, a food, a cosmetic product, a fertilizer, a building material, an adhesive, a bleach, a decalcifier, an autocare product, floorcare product, cookercare product, leathercare product or furniture care product, a scourer, a disinfectant, a fragrancer, a mold remover and/or a precursor of the aforementioned products.

The skilled person is fully aware of the applicability of perfume ingredients, and compositions to personal and house hold care compositions and a very detailed description of such compositions is not warranted here. However, specific compositions that can be mentioned include cleaning compositions; autocare compositions; Cosmetic compositions; textile treatment compositions; and air freshener and air care compositions.

Cleaning products include:—

Toilet cleaners or lavatory cleaners, in other words, products for cleaning lavatory bowls and urinals, these products being supplied preferably in the form of powders, blocks, tablets or liquids, preferably gels. Besides other typical ingredients such as surfactants, they generally include organic acids e.g., citric acid and/or lactic acid) or sodium hydrogen sulfate, amidosulfuric acid or phosphoric acid for removing limescale or urine scale;

Pipe-cleaning products or drain cleaners. These are typically strongly alkaline products which serve in general to remove pipe blockages comprising organic materials-such as hair, fat, food residues, soap deposits, and the like. Additions of Al powder or Zn powder may serve for the formation of H2 gas with an effervescence effect. Possible ingredients are commonly alkalis, alkaline salts, oxidizing agents, and neutral salts. Supply forms in powder form preferably also include sodium nitrate and sodium chloride. Pipe-cleaning products in liquid form may preferably also include hypochlorite. There are also enzyme-based drain cleaners as well. Acidic products are likewise possible;

Universal or all-purpose or general-purpose cleaners. These are cleaners which can be used universally for all hard surfaces in the household and in commerce that can be wiped down wet or damp. Generally speaking, they are neutral or slightly alkaline or slightly acidic products, especially liquid products. All-purpose or general-purpose cleaners generally contain surfactants, builders, solvents and hydrotropes, dyes, preservatives, and the like;

All-purpose cleaners with special disinfectant properties. They additionally include active antimicrobial ingredients (e.g., aldehydes, alcohols, quaternary ammonium compounds, amphoteric surfactants, triclosan);

Sanitary cleaners. These are products for cleaning in bath and toilet. The alkaline sanitary cleaners are used preferably for removing fatty soiling, whereas the acidic sanitary cleaners are employed in particular, for removing limescale. Sanitary cleaners advantageously also have a considerable disinfectant action, particularly the strongly alkaline sanitary cleaners that contain chlorine;

Oven cleaners or grill cleaners which may be supplied in the form of gels or foam sprays. They generally serve for removing burnt-on or carbonized food residues. Oven cleaners are preferably given a strongly alkaline formulation using, for example, sodium hydroxide, sodium metasilicate, 2-aminoethanol. In addition they generally contain anionic and/or nonionic surfactants, water-soluble solvents, and, in some cases, thickeners such as polycarboxylates and carboxymethylcellulose;

Metal polishes. These are cleaners for particular types of metal such as stainless steel or silver. Stainless steel cleaners preferably contain, besides acids (preferably up to 3% by weight, e.g., citric acid, lactic acid), surfactants (in particular, up to 5% by weight, preferably nonionic and/or anionic surfactants), and water, solvents as well (preferably up to 15% by weight) to remove fatty soiling, and also further compounds such as thickeners and preservatives. Very fine polishing structures are included, furthermore, in products for preferably bright stainless steel surfaces.

Silver polishes, in turn, may be provided in an acidic formulation. In particular, for removing black deposits of silver sulfide they contain, preferably, complexing agents (e.g., thiourea, sodium thiosulfate). Typical supply forms are polishing cloths, dipping baths, pastes, and liquids. Dark discolorations (oxide layers) are removed using copper cleaners and nonferrous-metal cleaners (e.g., for brass and bronze). They generally have a weakly alkaline formulation (preferably with ammonia) and in general contain polishing agents and also, preferably, ammonium soaps and/or complexing agents;

Glass cleaners and window cleaners. These products serve preferably to remove dirt, especially greasy dirt, from glass surfaces. Preferably they contain compounds such as anionic and/or nonionic surfactants (in particular, up to 5% by weight), ammonia and/or ethanolamine (in particular, up to 1% by weight), ethanol and/or 2-propanol, glycol ethers (in particular, 10-30% by weight), water, preservatives, dyes, anti-misting agents and the like; and Special-purpose cleaning products, examples being those for glass-ceramic hobs, and also carpet cleaners and stain removers.

Autocare products include:—

Paint preservers, paint polishes, paint cleaners, wash preservers, shampoos for auto washing, auto-wash and wax products, polishes for trim metals, protective films for trim metals, plastics cleaners, tar removers, screen cleaners, engine cleaners, and the like.

Cosmetic products include:—

(a) cosmetic skincare products, especially bath products, skin washing and cleansing products, skincare products, eye makeup, lip care products, nail care products, intimate care products, foot care products;

(b) cosmetic products with specific effects, especially sunscreens, tanning products, de-pigmenting products, deodorants, antiperspirants, hair removers, shaving products, perfumes;

(c) cosmetic dental-care products, especially dental and oral care products, tooth care products, cleaners for dental prostheses, adhesives for dental prostheses; and (d) cosmetic hair care products, especially hair shampoos, hair care products, hair setting products, hair-shaping products, and hair coloring products.

Textile treatment products include:—

Detergents or fabric conditioners, for example, in either liquid or solid form.

Air fresheners and room fragrancers include:—

Products that contain preferably volatile and usually pleasant-smelling compounds which advantageously can even in very small amounts mask unpleasant odours. Air fresheners for living areas contain, in particular, natural and synthetic essential oils such as pine needle oils, citrus oil, eucalyptus oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants. Other presentation forms include sticks and blocks. They are produced typically using a gel concentrate comprising essential oils. It is also possible to add formaldehyde (for preservation) and chlorophyll (preferably <5% by weight), and also further ingredients. Air fresheners are not, however, restricted to living spaces, but may also be intended for autos, cupboards, dishwashers, refrigerators or shoes, and even their use in vacuum cleaners is a possibility. In the household (e.g., in cupboards), for example, in addition to the odour improvers, disinfectants as well are employed, containing preferably compounds such as calcium phosphate, talc, stearin, and essential oils, these products taking the form, for example, of sachets.

The invention is now described with reference to the following non-limiting examples. These examples are for the purpose of illustration only and it is understood that variations and modifications can be made by one skilled in the art.

General: The compounds of the present invention have been prepared in one step by mixing a fragrant aldehyde and an amine. The reaction can be carried out without solvent at a temperature preferably between 65-80° C. under a pressure of 30-80 mbar and a reaction time of 3-7 h. Alternatively, the reaction is conducted in a round bottom flask together with molecular sieve (3-4 Å) under atmospheric pressure and at a temperature between 65-80° C. The products were used without further purification. NMR spectra were measured in CDCl$_3$ and are reported relative to TMS ($^1$H NMR) as follows: chemical shifts (δ ppm), coupling constants J in Hz. Solid probe MS analyses were run on a SSQ 7000 Thermo mass spectrometer and are reported as m/z list (relative intensity).

Example 1: Mixing Methyl 2-aminobenzoate and (E/Z)-9-hydroxy-5,9-dimethyldec-4-enal (Molar Ratio 1:1)

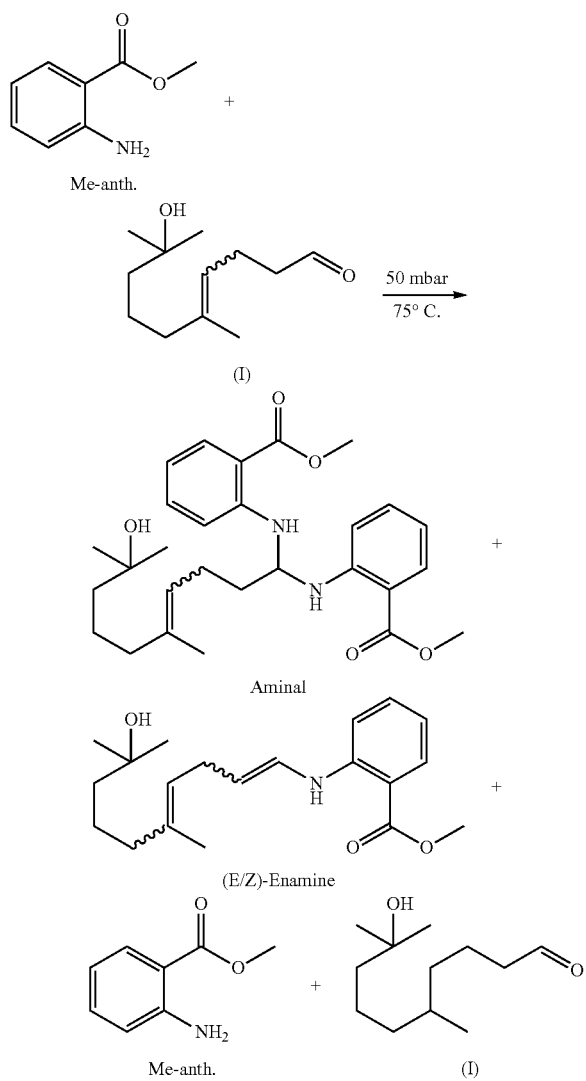

A mixture of methyl 2-aminobenzoate (1.51 g, 10.0 mmol) and (E/Z)-9-hydroxy-5,9-dimethyldec-4-enal (1.98 g, 10.0 mmol) was stirred at 75° C. and 50 mbar for 7 h to yield 3.32 g of a bright yellow oil. No purification was needed as the product will be used in perfumery applications as is. Analysis of the crude reaction mixture revealed two major components, "enamine" methyl 2-(((1E/Z, 4E/Z)-9-hydroxy-5,9-di methyldeca-1,4-dien-1-yl)amino)benzoate and "aminal" (E/Z)-dimethyl 2,2'-((9-hydroxy-5,9-dimethyldec-4-ene-1,1-diyl)bis(azanediyl))-dibenzoate (molar ratio enamine/aminal=2.4:1).

Methyl 2-(((1E/Z, 4E/Z)-9-hydroxy-5,9-dimethyl-deca-1,4-dien-1-yl)amino)benzoate $^1$H NMR (CDCl$_3$, 400 MHz); mixture of (1E/Z, 4E/Z) isomers: δ=9.69 (br d, J=10.5 Hz, NH), 9.66 (br d, J=10.5 Hz, NH), 9.53 (br d, J=10.2 Hz, NH), 9.52 (br d, J=10.5 Hz, NH), 7.93-7.87 (m, 4H), 7.38-7.29 (m, 4H), 6.94-6.88 (m, 4H), 6.70-6.61 (m, 4H), 6.51-6.45 (m, 4H), 5.25-5.07 (m, 6H), 4.65-4.57 (m, 2H), 3.87 (s, 3H), 3.87 (s, 3H), 3.84 (s, 3H), 3.82 (s, 3H), 2.92-2.87 (m, 4H), 2.79-2.75 (m, 4H), 2.13-1.91 (m, 8H), 1.72-1.64 (m, 12H), 1.48-1.36 (m, 16H), 1.21-1-17 (m, 24H) ppm. $^{13}$C NMR (CDCl$_3$, 100 MHz); mixture of (1E/Z, 4E/Z) isomers: δ=168.9 (s), 168.8 (s), 168.8 (s), 168.7 (s), 146.6 (s), 146.6 (s), 146.4 (s), 146.4 (s), 136.1 (s), 135.8 (s), 135.8 (s), 135.7 (s), 134.5 (d), 134.5 (d), 134.5 (d), 134.5 (d), 131.6 (d), 131.5 (3d), 125.1 (d), 125.0 (d), 123.5 (d), 123.3 (d), 123.1 (d), 122.9 (d), 122.7 (d), 122.3 (d), 116.4 (2d), 116.1 (d), 116.0 (d), 111.7 (d), 111.7 (d), 111.6 (d), 111.6 (d), 110.5 (s), 110.5 (s), 110.4 (s), 110.1 (s), 109.4 (d), 109.2 (d), 107.3 (d), 107.3 (d), 70.8 (s), 70.7 (s), 70.7 (s), 70.7 (s), 51.7 (q), 51.6 (q), 51.5 (q), 51.4 (q), 43.5 (t), 43.4 (t), 43.4 (2t), 39.9 (t), 39.9 (t), 32.0 (t), 31.9 (t), 29.1 (2q), 29.1 (4q), 29.1 (2q), 28.3 (t), 28.3 (t), 24.5 (t), 24.5 (t), 23.3 (q), 23.2 (q), 22.6 (t), 22.5 (t), 22.4 (2t), 15.9 (q), 15.7 (q) ppm. MS (EI); sum of (1E/Z, 4E/Z) isomers: 331 (25, [M]$^+$.), 316 (4), 244 (5), 230 (21), 198 (13), 190 (8), 178 (12), 177 (100), 158 (10), 151 (24), 146 (10), 145 (26), 119 (19), 92 (8), 77 (6).

(E/Z)-Dimethyl 2,2'-((9-hydroxy-5,9-dimethyldec-4-ene-1,1-diyl)bis(azanediyl))dibenzoate $^1$H NMR (CDCl$_3$, 400 MHz); mixture of E/Z isomers: δ=8.03 (br d, J=6.5 Hz, 4NH), 7.91 (dd, J=8.1, 1.5 Hz, 4H), 7.34-7.29 (m, 4H), 6.68 (d, J=8.6 Hz, 4H), 6.65-6.60 (m, 4H), 5.24-5.18 (m, 2H), 5.03-4.97 (m, 2H), 3.82 (s, 12H), 2.25 (quart, J=7.3 Hz, 4H), 1.99-1.92 (m, 8H), 1.68 (d, J=1.0 Hz, 3H), 1.51 (br s, 3H), 1.48-1.33 (m, 8H), 1.19 (s, 6H), 1.14 (s, 6H) ppm. $^{13}$C NMR (CDCl$_3$, 100 MHz); mixture of E/Z isomers: δ=168.8 (2s), 168.8 (2s), 149.4 (2s), 149.4 (2s), 136.6 (s), 136.6 (s), 134.6 (2d), 134.6 (2d), 131.7 (2d), 131.7 (2d), 123.6 (d), 122.8 (d), 115.3 (2d), 115.3 (2d), 111.8 (2d), 111.8 (2d), 110.7 (2s), 110.5 (2s), 70.8 (s), 70.7 (s), 62.5 (d), 62.3 (d), 51.5 (2q), 51.5 (2q), 43.5 (t), 43.4 (t), 40.0 (t), 35.7 (t), 35.4 (t), 31.9 (t), 29.2 (2q), 29.0 (2q), 23.7 (t), 23.6 (t), 23.2 (q), 22.5 (t), 22.5 (t), 15.7 (q) ppm. MS (EI); sum of E/Z isomers: 482 (2, [M]$^+$.), 332 (23), 331 (25, [M]$^+$.-.NH(C$_6$H$_4$)CO$_2$CH$_3$), 316 (8), 272 (4), 244 (12), 230 (38), 198 (17), 190 (10), 178 (13), 177 (100), 164 (20), 151 (64), 145 (30), 120 (18), 119 (56), 92 (25).

Odour description of the crude reaction mixture: floral muguet, natural, orange flower Example 2: Mixing Methyl 2-aminobenzoate and (E/Z)-9-hydroxy-5,9-dimethyldec-4-enal (Molar Ratio 2:1)

A mixture of methyl 2-aminobenzoate (3.02 g, 20.0 mmol) and (E/Z)-9-hydroxy-5,9-dimethyldec-4-enal (1.98 g, 10.0 mmol) was stirred at 75° C. and 50 mbar for 7 h to yield 4.73 g of a bright yellow oil. No purification was needed as the product will be used in perfumery applications as is. Analysis of the crude reaction mixture revealed two major components, "aminal" (E/Z)-dimethyl 2,2'-((9-hydroxy-5,9-dimethyldec-4-ene-1,1-diyl)bis(azanediyl))-dibenzoate and "enamine" methyl 2-(((1E/Z, 4E/Z)-9-hydroxy-5,9-dimethyldeca-1,4-dien-1-yl)amino)benzoate (molar ratio aminal/enamine=2:1).

Spectral data of (E/Z)-dimethyl 2,2'-((9-hydroxy-5,9-dimethyldec-4-ene-1,1-diyl)bis(azanediyl))-dibenzoate and methyl 2-(((1E/Z, 4E/Z)-9-hydroxy-5,9-dimethyldeca-1,4-dien-1-yl)amino)-benzoate are reported in Example 1.

Odour description of the crude reaction mixture: floral orange flower, methyl anthranilate, muguet Example 3: Preparation of a Feminine Oriental Fine Fragrance

| Compound/Ingredient | parts by weight 1/900 |
| --- | --- |
| cis-3-Hexenyl acetate | 3 |
| Isoeugenyl acetate | 25 |
| Phenyl acetic acid (at 1% in DPG) | 3 |
| 1,2,3,4,4a,5,6,7-Octahydro-2,5,5-trimethyl-2-naphthalenol (Ambrinol) (at 1% in DPG) | 35 |
| Ambrofix (at 10% in DPG) | 2 |
| Animalis 1745 subst. PMF 2 | 15 |
| 2-Ethoxy-9-methylen-2,6,6-trimethylbicyclo [3.3.1]-nonane (Boisiris) | 20 |
| l-(2,6,6-Trimethyl-2-cyclohexen-1-yl)-1,6-heptadien-3-one (Cetone V) | 3 |
| Coumarin | 20 |
| (2E)-1-(2,6,6-Trimethyl-1-cyclohexen-1-yl) but-2-en-1-one (Damascone beta) (at 10% in DPG) | 8 |
| 2,6-Dimethylheptan-2-ol (Dimetol) (at 10% in DPG) | 25 |
| 2-Ethyl-3-hydroxy-4-pyranone (Ethyl Maltol) (at 1% in DPG) | 14 |
| 3-Ethoxy-4-hydroxybenzaldehyd (Ethylvanillin) | 15 |
| Ethyl 2-ethyl-6,6-dimethyl-2-cyclohexenecarboxylate & Ethyl 2,3,6,6-tetramethyl-2-cyclohexenecarboxylate (Givescone) | 100 |
| Methyl 2-(3-oxo-2-pentylcyclopentyl) acetate (Hedione) | 250 |
| 1,3-Benzodioxole-5-carbaldehyde (Heliotropine) | 4 |
| cis-3-Hexenol | 3 |
| Indolene 50%/Castor oil | 20 |
| 3-Methyl-4-(2,6,6-trimethylcyclohex-2-en-1-yl)but-3-en-2-one (Isoraldeine 95) | 25 |
| Patchouli Ess. | 20 |
| 2-Ethyl-4-(2,2,3-trimethylcyclopent-3-en-1-yl)but-2-en-1-ol (Radjanol) | 45 |
| 4-(4-Hydroxyphenyl)butan-2-one (Raspberry Ketone) | 5 |
| 4-Methyl-2-(2-methylprop-1-enyl) tetrahydro-2H-pyran (Rose Oxide) | 3 |
| 2-[1-(3,3-Dimethylcyclohexyl) ethoxy]-2-methylpropyl cyclopropanecarboxylate (Serenolide) | 45 |
| Methyl Cedryl Ketone | 55 |
| Dipropylene glycol (DPG) | 82 |
| Product from Example 1 | 55 |
| Total: | 900 |

The addition of the reaction mixture comprising at least methyl 2-((-9-hydroxy-5,9-dimethyldeca-1,4-dien-1-yl) amino)-benzoate and dimethyl 2,2'-((9-hydroxy-5,9-dimethyldec-4-ene-1,1-diyl)bis(azanediyl))-dibenzoate as prepared in Example 1 reinforces the floral character of the composition and provides an orange flower facet and at the same time adds volume and performance to the whole composition. It blends very well with Hedione, Indolene and Patchouli and gives a subtle sensuality to this oriental feminine fine fragrance.

The invention claimed is:

1. A fragrance precursor of (E/Z)-9-hydroxy-5,9-dimethyldec-4-enal, comprising at least an enamine and/or an aminal as reaction product of (E/Z)-9-hydroxy-5,9-dimethyldec-4-enal and a primary and/or secondary amine.

2. The fragrance precursor according to claim 1, wherein the primary and/or secondary amine is selected from the group consisting of:
aromatic amines;
primary or secondary aliphatic amines;
etheramines;
ethylene- and propylene-amines;
amino acids and derivatives;
polyamines; N-(3-aminopropyl)imidazole, nipecotamide, skatole and indole.

3. The fragrance precursor of claim 2, wherein the aromatic amine is selected from: methyl 2-aminobenzoate (methyl anthranilate), 2-amino-acetophenone, ortho, meta or para aminobenzoates of formula II

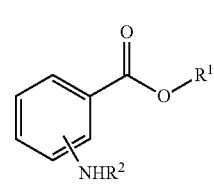

Aminobenzoates wherein:
R1=C1-C12 linear or branched alkyl, alkenyl, cycloalkyl, cycloalkenyl or alkylaryl and,
R2=H, Me, or Et.

4. The fragrance precursor of claim 2, wherein the primary or secondary aliphatic amines are selected from: C8-C30 linear or branched alkylamines or alkyldiamines.

5. The fragrance precursor of claim 2, wherein the polyamines are selected from: primary and secondary polyetheramines, polyethyleneimines, polypropyleneimines, polyamidoamines, polyamino acids, polyvinylamines, poly (ethylene glycol) bis(amine) and amino substituted polyvinylalcohols.

6. The fragrance precursor according to claim 2, comprising at least one of:
methyl 2-(((1E/Z, 4E/Z)-9-hydroxy-5,9-dimethyldeca-1,4-dien-1-yl)amino)benzoate; and,
(E/Z)-dimethyl 2,2'-((9-hydroxy-5,9-dimethyldec-4-ene-1,1-diyl)bis(azanediyl))dibenzoate.

7. The fragrance precursor according to claim 2 which is odiferous and which is a perfume ingredient.

8. A method of imparting a muguet odour characteristic to a personal care composition or household care composition, the method comprising the step of:
including a fragrance precursor according to claim 2 in the personal care composition or household care composition.

9. A method of imparting a muget odour characteristic to a perfume composition comprising the step of:
adding to said composition at least a fragrance precursor according to claim 2.

10. The fragrance precursor according to claim 1, comprising: at least one of:
methyl 2-(((1E/Z, 4E/Z)-9-hydroxy-5,9-dimethyldeca-1,4-dien-1-yl)amino)benzoate, and,
(E/Z)-dimethyl 2,2'-((9-hydroxy-5,9-dimethyldec-4-ene-1,1-diyl)bis(azanediyl))dibenzoate.

11. The fragrance precursor according to claim 1 which is odiferous and which is a perfume ingredient.

12. The fragrance precursor according to claim 11, wherein perfume ingredient releases muguet odour characteristics.

13. A perfume composition comprising a fragrance precursor according to claim 1.

14. The perfume composition according to claim 13 that is substantially free of 4(4-hydroxy-4-methylphenyl) 3-cyclohexane carboxaldehyde.

15. The perfume composition according to claim 13 which further comprises: (E/Z)-9-hydroxy-5,9-dimethyldec-4-enal.

16. The perfume composition according to claim 13, which further comprises one or more additional fragrance ingredients.

17. The perfume composition according to claim 13, which is adapted to release an ingredient with muguet odour characteristics.

18. A personal care or household care composition comprising at least a fragrance precursor according to claim 1.

19. A method of imparting a muguet odour characteristic to a perfume composition comprising the step of:
adding to said composition at least a fragrance precursor according to claim 1.

20. A method of imparting a muguet odour characteristic to a personal care composition or household care composition, the method comprising the step of:
including a fragrance precursor according to claim 1 in the personal care composition or household care composition.

* * * * *